(12) United States Patent
Liu

(10) Patent No.: US 8,114,444 B2
(45) Date of Patent: Feb. 14, 2012

(54) **PHARMACEUTICAL COMPOSITION CONTAINING *MOMORDICA CHARANTIA* L. EXTRACTS FOR LOWERING BLOOD GLUCOSE**

(76) Inventor: Yaguang Liu, Tuckerton, NJ (US)

( * ) Notice: Subject to any disclaimer, the term of this patent is extended or adjusted under 35 U.S.C. 154(b) by 367 days.

(21) Appl. No.: 12/589,562

(22) Filed: Oct. 26, 2009

(65) Prior Publication Data

US 2011/0097415 A1    Apr. 28, 2011

(51) Int. Cl.
*A61K 36/00* (2006.01)
*A61K 9/22* (2006.01)

(52) U.S. Cl. ......... 424/725; 424/457; 424/458; 424/461

(58) Field of Classification Search ........................ None
See application file for complete search history.

(56) References Cited

U.S. PATENT DOCUMENTS

| 4,985,248 | A | * | 1/1991 | Liu | 424/758 |
| 5,086,043 | A | * | 2/1992 | Liu | 514/25 |
| 5,098,710 | A | * | 3/1992 | Liu | 424/758 |

FOREIGN PATENT DOCUMENTS

| CN | 1303698 A | * | 12/1999 |
| CN | 101406479 A | * | 4/2009 |

* cited by examiner

*Primary Examiner* — Patricia Leith
(74) *Attorney, Agent, or Firm* — Yaguang Liu

(57) ABSTRACT

The present invention is providing a new sustained release drug preparation comprising such and inclusion complex of a medical compound with safe botanic drug (SBD), which sustains or retards the dissolution and release of the SBD at a controlled rate from the inclusion complex and hence from the drug preparation containing the SBD, so as to maintain the concentration of the SBD in blood at an effective level for prolonged time.

SBD contains Kuguasu (KU) and saponins of Kugua (SAK). SBD is very safe and it is used for treating and preventing diabetes.

11 Claims, No Drawings

PHARMACEUTICAL COMPOSITION CONTAINING *MOMORDICA CHARANTIA* L. EXTRACTS FOR LOWERING BLOOD GLUCOSE

DESCRIPTION OF THE PRIOR ART

The major characteristic of diabetes is the body's inability to regulate the level of glucose in the blood. Therefore, the goal of treating diabetes is the reduction the blood glucose. In clinic, insulin and some oral hypoglycemic drugs, which include tolbutamide, tolazamide, acetohexamide, chlorpropamide, glyburide and glipizide, are available for treating diabetes. However, all mentioned above drugs have several disadvantages in therapeutic use. For example, some drugs increase the risk of acute cardiovascular disease. All drugs are not effective in treating the following symptoms: diabetic acidosis or in stressful situations such as infection and the degenerative diseases which cause by diabetes. More particularly, as mentioned earlier drugs are not effective in treating atherosclerosis, loss of sight, morbidity and death brought about by progressive vascular injury.

DETAILED DESCRIPTION

Diabetes is a disease that affects at least five percent of the America population. It is the third leading cause of death in the United States. The annual incidence of diabetes is 620,000. Nearly 10 percent of working persons age 45 or older are diabetics.

It is estimated that around 250 million people are living with diabetes today and this number will increase to around 380 million by 2025.

Diabetes has become a major cause of premature illness and death in most countries, mainly through the increased risk of cardiovascular disease. In 2005, an estimated 1.1 million people around the world died directly from diabetes. The number of people whose death was recorded as heart disease or kidney failure where diabetes was a contributory factor is, however, considerably higher. Each year, diabetes related causes account for 3.8 million deaths.

The prevention and treatment of diabetes and its complications cost around US$232 billion in 2007. By 2025, the cost is likely to exceed US$302.5 billion. In the US, the total economic cost of diabetes was estimated to be US$174 billion in 2007, of which US$116 billion was medical expenditure; US$27 billion was for diabetes care, US$58 billion was for chronic complications related to diabetes, and US$31 billion was attributed to general medical costs.

It is estimated that the global diabetes therapy market at around US$26.3 billion in 2009. By 2013, the market is expected to grow to around US$34.5 billion. Oral diabetes drugs account for around 39% of the total market value.

The present invention related to pharmaceutical compositions is a formulation of pure sustained release oral dosage micropellets in a capsule which contains sustained release of botanic drug (SBD) when taken by a patient and are comprised of inner seeds coated with SBD. The oral dosage formulation is administered by the capsule and placing the micropellets on drug. A delay in absorption was found significantly.

There is thus a need for a slow-release SBD composition which provides satisfactory bioavailability and absorption pattern when taken orally with drug.

The oral sustained release SBD formulation of the present invention provides a means to administer SBD in a micropellet formulation which enables patients to receive the correct therapeutic blood level of SBD.

The micropellets of this invention are utilized in an easily openable capsule containing a sufficient amount of micropellets to provide a dosage unit of SBD. The dosage unit administered to a patient is determined by the age, size and condition of the patient as well as the severity of the disease.

Safe botanic drug (SBD) includes two ingredients: Kuguasu (KU) and saponins of Kugua (SAK). KU and SAK are extracted from *Momordica charantia* L which is a vegetable in market of US. The approximate % in weight in SBD are listed below:

| Compound | Approximate concentration in weight percent in SBD | Preferred composition weight percent |
| --- | --- | --- |
| KU | 20-80 | 50 |
| SAK | 20-80 | 50 |

Diabetes is a state of absolute or relative lack of functional insulin. It is not a single disease in the classic sense; but rather a clinical syndrome applied to a number of Pathogenetically heterogenous disorders. To be exact, Diabetes is disease characterized by abnormalities of the endocrine secretions of the pancreas resulting in disordered metabolism of carbohydrate, fat and protein, and in time, structural and functional abnormalities in a variety of tissues. It also has been established in the prior art that metabolism of carbohydrate, fat, protein and hormones, et al are regulated by liver. The liver plays a key role in regulation metabolism of carbohydrate (including glucose) and is important in many other bodily functions. It manufactures blood coagulants, stores vitamins and minerals, produces enzymes, cholesterol and proteins and neutralizes substances that would harm the body. The liver can construct the storage form of many energy sources, for example, glycogen and fats. The liver can also convert glucose to protein and fat, protein into glucose, and fat into protein or glucose. Obviously, the liver plays a key role in relation metabolism of diabetes.

For the reason given above, "SBD" which can reduce blood glucose and repair disordered metabolism including increasing synthesis of RNA and protein in injured liver at same time, it is very important for treating and preventing diabetes.

In addition, the composition is very safe because SBD is extracted from vegetables. SBD can be administered to patients in the form of capsules containing a powdered mixture of the active ingredients in appropriate proportions. Alternatively, tablets can be prepared comprising the active ingredients and pharmaceutically acceptable binders, excipients, lubricants, sweeteners and coatings. A syrup or elixir may be prepared by dissolving the composition in alcohol or water together with suitable preservatives, sweeteners, dyes and flavoring agents. Ampoules or vials for injection may likewise be prepared, with the composition as prepared for oral administration being purified through further sterilization and the addition thereto of distilled water and other suitable solvents and additive known in the pharmaceutical art.

The composition dosage units prepared according to the invention can be administered to patients with a very safe and in reducing blood glucose and repairing disorderly metabolism.

The following specific examples will provide detailed illustrations of methods of producing composition according to the present invention and pharmaceutical dosage units containing composition. Moreover, examples will be given of pharmaceutical testing performed with composition that demonstrates its effectiveness in treating and preventing diabetes. These examples are not intended, however, to limit or restrict the scope of the invention in any way, and should not be construed as providing conditions, parameters, reagents, or starting materials which must be utilized exclusively in order to practice the present invention.

EXAMPLE 1

1 kg polyvinylpyrrolidone (PPD) (molecular weight 40.000) were dissolved in 10 liter of isopropand, and 1 kg of micronized SBD were dispersed in there. 3.5 kg of sugar was placed in suspension and mix. SBD is coated onto the sugar seed by first combining it with a water soluble system such as polyethylene glycol or polyvinylpyrrolidone.

The resulting SBD coated sugar seeds are then coated with a pharmaceutically acceptable water insoluble system such as ethylcellulose, cellulose acetate butyrate or cellulose triacetate, with ethyl cellulose preferred. This coating enables release of the SBD. The average diameter of each of the finished micropellets is about 0.4 to 0.6 mm, preferably about 0.5 mm. This provides a coating with a sufficient amount of channels to enable the SBD to be released.

The dissolution rate depends on the weight of the micropellets and solvent system. The pellets were screened.

As desired, the final coated products containing an ethylcellulose coating level of 1% was prepared. The pellets were dried under vacuum.

The products contained 99.0% by weight of SBD and 1% by weight ethylcellulose coating.

EXAMPLE 2

Plasma concentration of SBD in rat was determined by regular methods.

TABLE 2

| Plasma Concentrating of SBD | | |
|---|---|---|
| | Regular preparation of SBD | Sustained release of SBD |
| 1 h | 120 mg/ml | 92 mg/ml |
| 4 h | 92 mg/ml | 80 mg/ml |
| 8 h | 65 mg/ml | 63 mg/ml |
| 24 h | 24 mg/ml | 32 mg/ml |
| 48 h | 15 mg/ml | 25 mg/ml |
| 72 h | 8 mg/ml | 20 mg/ml |

The data in table shows that plasma concentration of SBD in sustained preparation was not significantly different from SBD in regular preparation before 8 hours. But it did after 8 hours. The data shows that bioavailability of sustained release preparation of SBD is better than regular preparation of SBD.

EXAMPLE 3

The formation of an inclusion complex of a medical compound with SBD in accordance with the process described above was confirmed by various methods such as powder X-ray diffraction, dissolution behavior, scanning electron microscope analysis, differential thermal analysis (DTA) and infrared absorption (IR). Inclusion complexes were prepared using SBD as a medical compound, and the behavior of dissolution and release of SBD from the inclusion complex in the capsule form, as well as the behavior of dissolution and release of SBD from compressed capsule containing the inclusion complex were determined.

The characteristic peaks of the individual components have disappeared, but instead, such a diffraction pattern which is different from the diffraction patterns of a physical mixture of both the components has been given. These results of the X-ray diffraction patterns support the fact that SBD and a pharmaceutical acceptable have complex with each other and formed an inclusion complex of them having a structure different from the original structures of the individual components.

EXAMPLE 4

To demonstrate the behaviors of dissolution and release of the medical compound from the sustained release pharmaceutical composition according to this particular embodiment of this invention, the following tests were conducted. Thus, an inclusion complex of SBD shows a highly controlled release rate of the tablet samples. The respective tablet samples were separately placed into water and release into water from the tablet was determined with lapse of time which exhibits a similar variation in the amount of SBD as dissolved and released from a tablet sample. It is observed that the SBD was absorbed promptly into the blood and disappeared quickly from the blood when the original tablet which is mixture of SBD with starch in the compressed tablet form was orally given, and that in contrast, pure sustained release of SBD was maintained in the blood at substantially steady concentrations for prolonged period of time.

EXAMPLE 5

The novelty of the present invention resides in the mixture of the active ingredients in the specified proportions to produce SBD and in the preparation of dosage units in pharmaceutically acceptable dosage form. The term "pharmaceutical acceptable dosage form" as used hereinabove includes any suitable vehicle for the administration of medications known in the pharmaceutical art, including, by way of example, tablets, capsules, syrups, and elixirs with specified ranges of SBD concentration.

EXAMPLE 6

Hypoglycemic Effect of Composition

Experiments use alloxan diabetic mice. Male mice 18-22 g was used in these experiments. The diabetic mice had high blood glucose, produced by a single dose of alloxan 75 mg/kg intravenously. Inject 2 ml of normal saline into the peritoneal cavity of mouse for control and 100 mg/kg composition group daily. Blood samples were collected from ocular venous plexus of mice.

The blood glucose levels were determined according to hexokinase method. The procedure is as the following:
A. Reagents
1. Vial B, containing NADP. Reconstitute by adding 15.5 ml water and gently swirling.
2. Vial A. Add the entire contents of vial B to vial A and dissolve by gently inversion.
According to the manufacturer, the reagent has the following composition:
a. Tris buffer, pH 7.5, 50 mmol/L
b. ATP, 0.5 mmol/L
c. $NADP^+$, 0.45 mmol/L
d. $Mg^{++}$, 17 mmol/L e. Hexokinase, 666 U/L
f. G6PD, 333 U/L
3. Stock Standard Glucose, 10.0 g/L. Dissolve 1.0 g pure anhydrous D-glucose in water containing 1.0 g benzoic acid per liter. Make up to 100 ml volume in the benzoic acid solution.
4. Working Glucose Standards. Prepare standards of 50, 100, 200, and 400 mg/dl by appropriate dilution of Stock Standard with benzoic acid solution.

B. Procedure

1. Place 1.5 ml prepared reagent in a series of cuvets for standard, unknowns, and control serum, respectively.
2. Appropriate blanks are set up by placing 1.5 ml of 9 g/L NaCl in a series of cuvets.
3. After incubating for 5 or 10 minutes, read the absorbance of each cuvet at 340 nm and check again a few minutes later to insure that an end point has been reached.

TABLE 1

| Blood glucose level (mg/dl) | | |
| --- | --- | --- |
| C | SBD | BD |
| 251 ± 50 | 155 ± 17 | 162 ± 22 |

Number of samples: 20; $P < 0.01$; C: Control group; BD is regular formulation of botanic drug; SBD is sustained release formulation of botanic drug.

From above results, it is apparent that SBD and BD can obviously decrease blood glucose levels. Curative effects of SBD and BD are the same.

EXAMPLE 7

Effect of Composition on Binding Insulin Receptor

Rats were sacrificed by a blow on the head, and their epididymal adipose tissue were quickly removed. The fat cells were isolated from the adipose by the procedure of Rodbell (Rodbell, M.: J. Biol Chem, 239:375, 1964). In dulbecco buffer PH 7.4 containing collagenase (3 mg/ml) and albumin (40 mg/ml).

$^{125}$I-labeled insulin ($^{125}$I-insulin) was at specific activities of 100-200 µCi/µg. IgG was prepared from heparinized plasma. The IgG fraction of serum from the patient with the highest concentration of antireceptor antibody activity (B-2) was prepared from the ammonium sulfate precipitate by ion exchange chromatography of DEAE-cellulose. Antireceptor antibodies were assayed by methods of inhibition of $^{125}$I-insulin binding to cultured human lymphoblostoid cells. The cells were prepared: 2-4.times.10.sup.6 cells/ml of adipocytes cells were washed three times for 10 minutes at 37° C. and nondissociable radioactivity was extracted in 1% triton X-100.

$^{125}$I-insulin binding to isolated rat adiposytes were performed at 37° C. in krebs-ringer bicarbonate medium (PH 7.4) containing bovine serum albumin and bacitracin (100 U per milliliter). After adipocytes had been incubated with $^{125}$I-insulin for 30 minutes at 37° C., the cells were precipitated from the medium by centrifugation. The radioactivity in the pellet was counted.

TABLE 2

| The binding of insulin receptor | | |
| --- | --- | --- |
| C | SBD | BD |
| 100% | 135 ± 30 | 127 ± 18 |

Number of samples: 20; $P < 0.05$

From above results, it is apparent that SBD and BD can obviously stimulate binding insulin receptor with insulin. Bioeffects of SBD and BD are the same.

EXAMPLE 8

Effect of Composition on Synthesis of Protein

The 20-22 g male mice were used in experiments. The mice were injected with CCl.sub.4. The dosage of composition was 75 mg/kg injected intraperitoneally. The control mice were injected with same volume of normal saline. The mice were sacrificed by decapitation. Their liver was quickly excised and placed immediately in cold Medium which consisting of 0.25M sucrose, 0.065M potassium chloride, 0.035M potassium bicarbonate, 0.01M magnesium chloride and 0.05M tris (hydroxymethyl) aminomethane (Tris), adjusted to pH to 7.5 with HCl. The liver was cleaned of excess fat before the wet weight was measured. The liver from each animal was homogenized in each experiment. All operations were performed at 4.degree. C. Each liver was homogenized in 10 ml of cold Medium, Using Teflon and glass homogenizer immersed in ice. The homogenate was centrifuged at 1000 g for 10 minutes to remove large cellular particles. The resulting supernatant fluid was filtered through four layers of cloth to remove as much fatty material as possible. The filtrate was centrifuged at 37,000 g for 30 minutes. The sediment was discarded, and the resulting postmitochondrial fraction was used for the assay of translation. Protein concentration was measured by the biuret procedure [J. Biol Chem 177:751, 1949], using crystalline bovine serum albumin as a standard. The rate of translation was determined in an assay system containing: 0.2 ml of 0.01M ATP, 0.2 ml of 0.05M phospho puruvate, 0.05 ml of a $^3$H-amino acid mixture (containing approximately $5 \times 10^6$ cpm), 0.05 ml of crystalline pysuvate kinase (1 mg/ml), 0.1 ml of water and 1.0 ml of the postmitochondrial preparation in Medium in a total volume of 2 ml. The postmitochondrial preparation was added last to initiate the reaction, and the mixture was incubated for 30 minutes at 37° C. Under the conditions of the experiment, translation was a straight-line function of time for at least 45 minutes. The course of the reaction was halted by the addition of 5 ml of 10% trichloroacetic acid (TCA). Control tubes were prepared by adding all of the components of the reaction mixture into 5 ml of 10% TCA. The precipitated proteins were collected on a 0.45-µm membrane filter, using vacuum filtration. The collected precipitate was washed two times with 20 ml portions of 10% TCA and dried in an oven at 80° C. for 10 minutes. The dried filters were placed in scintillation vials containing 20 ml of Aquasol, and the radioactivity that had been incorporated into protein was measured in a liquid scintillation counter.

TABLE 3

| CPM/mg proteins | | |
| --- | --- | --- |
| C | SBD | BD |
| 560 ± 75 | 905 ± 130 | 976 ± 120 |

Number of samples: 20; P < 0.01

The data of Table 3 indicated that SBD and BD could increase protein synthesis of liver. Bioeffects of SBD and BD are the same.

EXAMPLE 9

The Effects of Composition on Ribonucleic Acid (RNA)

The method of animal is like procedure of example 8. 3H-uridine (10 µCi/100 g body weight) was injected intraperitoneally into mice 20 minutes prior to sacrifice. Their liver was quickly excised. Livers were washed with cold 0.25M sucrose containing 3.3 mM CaCl2 and minced with scissors. The mince was then homogenized with 3 volumes of the same solution in a Potter's homogenizer with a glass pestle and centrifuged at 1000.times.g for 10 minutes. The sediment was homogenized with 3 volumes of 0.25M sucrose-3.3 mM CaCl.sub.2 in a Potter's homogenizer with a Teflon pestle. The homogenates were filtered through 4 layers of gauze. Eight volumes of 2.2M sucrose was added and the mixture was centrifuged at 40000.times.g for 1 hour to sediment the nuclei. Purified nuclei were washed with 0.6N perchloric acid, ethanol and ether. To the residues was added 0.5N KOH and the mixture was incubated at 370 C. for 18 hours, followed by acidification to remove deoxyribonucleic acid (DNA) and proteins as precipitates. After centrifugation the supernatant was neutralized with KOH. Radioactivity incorporated into nuclear RNA and the amount of RNA was determined using aliquots of this supernatant. Radioactivity was counted in a scintillation spectrometer with solution, the composition of which was as follows: one liter of the solution contained 50 ml of methanol, 10 ml of ethyleneglycol, 60 g of naphthalene, 4 g of 2,5-diphenyloxazole, 0.2 g of 1,4-bis[2 (5phenyloxaxolyl)]-benzene and dioxane.

TABLE 4

| Specific radioactivity (CPM/mg RNA) | | |
| --- | --- | --- |
| C | SBD | BD |
| 18090 ± 1819 | 28900 ± 3200 | 25825 ± 2518 |

Number of samples: 20; P < 0.01

The data of Table 4 indicated that SBD and BD could obviously increase RNA synthesis. Bioeffects of SBD and BD are the same.

EXAMPLE 10

Safety of SBD (1): Toxic Dose for Mice

Methods for Determination of $LD_{50}$

Mice were used in the experiment. The animals were assigned by weight into the treatment and control groups. The animals were singly housed in hard-bottomed polypropylene cages with wood shavings. The animals had free access to food and water. Lighting was controlled on a 12 hours light; 12 hours dark cycle, (lights on 8 a.m.; lights off 8 p.m.). The housing facility temperature was maintained at 20°±2°. Humidity was maintained between 50-70%.

Parameters Assessed

Bodyweight, food and water intake. Prior to commencement of the study, all anima Is were weighed and assigned to groups, ensuring all groups had a similar mean weight. The body-weight of each animal was recorded prior to drug administration, as was food and water. These values were recorded again 24 hours later and the body-weight change, food and water intake was calculated as the difference between these three measurements.

Home cage activity. Animals were singly housed in a home cage monitor and their activity monitored during the nocturnal period (8 p.m.-8 a.m.), throughout the study. The cage in which the animal is housed (home cage) is placed into a compartment on a rack. On the top of each compartment there is a passive infra-red (PIR) sensor. The sensor is powered by a 10 volt direct current power supply. This splits the infra-red beam into 16 zones which radiate across the floor of the cage. The 24 sensors are connected by separate switch inputs to an interpak 2 interface. The whole system is controlled by the home cage activity monitor software package. The data are listed as below.

$LD_{50}$: The LD50 of SBD in mice (I.P.) was found to be 2.5 g/kg.

Toxic doses for mice: In 38 normal mice after injection of SBD of 2.5 g/kg/day×5 with the observation period of 5 days none of the mice died.

As to subacute toxicity tests, a dosage corresponding to 50 times the clinical dose is administered continually for two months, and no side effects have been observed. The electrocardiograms and functions of liver and the kidney have not been affected and no injuries whatever have been observed in the tissue slices of the heart, liver, spleen, lungs, kidneys and adrenal.

EXAMPLE 11

Safety of SBD(2): Mutagenic Effect of SBD

Determination of the mutagenic and carcinogenic activity is important for estimating side effects of drug. The mutagenic activity of many drugs can only be detected with growing cells. In present study, mutagenic and carcinogenic activity of SBD is determined by Bacteria system.

The method for detecting mutagenicity of SBD, with the Salmonella system that detects the reversion of the bacteria from His– to His+, is widely used.

Methods for detecting carcinogens and mutagens with the salmonellia mutagenicity test are highly efficient in detecting carcinogens and mutagens. Major carcinogens tested have been detected as mutagens. Salmonella mutagenicity assay is very sensitive and simply test for detecting mutagens and carcinogens. Therefore, it has been useful in a detailed study that has been made of mutagenic activity of SBD.

TA97 and TA100 are extremely effective in detecting classes of carcinogens and mutagenesis.

Methods

The bacterial tester strains used for mutagenesis testing are TA97 and TA100. Mutagenesis testing method was done as described previously. In brief, TA97 and TA100 were grown in agar gel culture. The petri plats (100×15 mm style) contain 30 ml with 2% glucose. The agar mixture was agitated vigorously and immediately poured into plates of minimal agar. The cultures were incubated at 37° C. in a dark and 5% CO2 in air for 48 hours. After 48 hours the colonies in both test and controls are counted. The presence of a background lawn of bacteria on the histidine-poor soft agar plate was used as an indication that gross toxic effects were absent. Mutagenicity assays were carried out at least in triplicate.

Results and Discussion

The data of experiment summarized as the following table.

TABLE 5

| Treatment | Dose/plate (µg) | Number of His+ revertants/plate | | | |
|---|---|---|---|---|---|
| | | TA97 | | TA100 | |
| | | −S | +S | −S | +S |
| Spontaneous | — | 149 ± 15 | 150 ± 17 | 120 ± 17 | 120 ± 15 |
| 4NQO | 0.5 | 861 ± 79 | — | 2301 ± 190 | — |
| SBD | | 186 ± 18 | 178 ± 19 | 150 ± 17 | 156 ± 16 |

*4QO: 4-nitroquinoline-1-Oxide

The salmonella typhimurium strains TA97 and TA100 were checked using 4-nitroquinoline-1-oxide. The range of spontaneous mutation rates for the individual strains, which were considered to be acceptable, was TA97 (100-170) and TA100 (80-150).

The data of Table 9 indicated that the number of His+ revertants/plate of SBD almost is as same as spontaneous of testing strains. On the contrary, 4NQO is mutagenic and carcinogenic agent. The number of His+ revertants/plate of 4NQO is higher than 10 times of spontaneous.

In conclusion, SBD has no carcinogenic and mutagenic action.

EXAMPLE 12

Production of Kuguasu

The fruits of *Momordica charantia* L. are dried and powdered. Five liters of 90% of ethanol are added to 1 kilogram of the powder to extract Kuguasu therefrom. The ethanol mixture is adjusted to pH 2.5 by addition of hydrochloric acid. The ethanol mixture is stirred and centrifuged to recover a clear extract. A 50% zinc chloride solution, $ZnCl_2$ is added to the extract and the extract is adjusted to pH 6.8 by addition of ammonium hydroxide, $NH_4OH$. A precipitate of Kuguasu is formed and separated by centrifuging. This precipitate is dissolved in an acidic aqueous solution. NaCl solution is added to the acidic solution to form a second precipitate of Kuguasu, which is washed with acetone, dried under vacuum, and powdered.

The preparation of composition is simple and can be accomplished by the extraction methods set forth above or any conventional methods for extracting the active ingredients. The novelty of the present invention resides in the mixture of the active ingredients in the specified proportions at invention and in the preparation of dosage units in pharmaceutically acceptable dosage form. The term "pharmaceutically acceptable dosage form" as used hereinabove includes any suitable vehicle for the administration of medications known in the pharmaceutical art, including, by way of example, tablets, capsules, syrups, elixirs, and solutions for parenteral injection with specified ranges of composition.

It will thus be shown that there are provided compositions and methods which achieve the various objects of the invention, and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by letter patent is set forth in the appended claims:

1. A sustained release pharmaceutical in the form of micro pellets for treating diabetes, wherein said pharmaceutical consists of 20-80% Kuguasu (KU) by weight of the pharmaceutical, 20-80% saponins of Kugua (SAK) by weight of the pharmaceutical, polyvinylpyrrolidone, isopropanol and a coating selected from ethyl cellulose, cellulose acetate butyrate and cellulose triacetate; wherein said SAK are extracted from *Momordica charantia* L; wherein said micro pellets have an average diameter of about 0.4 to 0.6 mm; and wherein said sustained release formulation is prepared by combining polyvinylpyrrolidone and isopropanol with a micronized formulation of KU and SAK to create a mixture, combining the mixture with sugar to create a second mixture and coating the second mixture with one of ethyl cellulose, cellulose acetate butyrate or cellulose triacetate to create the sustained release pharmaceutical micro pellets.

2. The pharmaceutical composition of claim 1, wherein KU and SAK are both present at 50% by weight of the sustained release pharmaceutical.

3. A pharmaceutical preparation, wherein said pharmaceutical preparation is in the form of a tablet, capsule or elixir and wherein said pharmaceutical preparation comprises the sustained release pharmaceutical of claim 1.

4. The pharmaceutical preparation of claim 3 in the form of a tablet.

5. The pharmaceutical preparation of claim 4, wherein said composition further comprises additional ingredients selected from the group consisting of binders, excipients, lubricants, sweeteners and coatings.

6. The pharmaceutical preparation of claim 3 in the form of a capsule.

7. The pharmaceutical preparation of claim 6 further comprising additional ingredients selected from the group consisting of preservatives, sweetening agents and flavoring agents.

8. The pharmaceutical preparation of claim 3 in the form of an elixir.

9. The pharmaceutical composition of claim 3 wherein said pharmaceutical preparation is in the form of a syrup or elixir and wherein the composition further comprises:
    a) water or alcohol and
    b) ingredients selected from preservatives, sweeteners, dyes and flavoring agents.

10. A method for preparing a pharmaceutical composition, said method comprising:
    a. dissolving 1 Kg polyvinylpyrrolidone in 10 liters of isopropanol,
    b. adding 1 Kg of a micronized mixture of Kuguasu (KU) and saponins of Kugua (SAK) to the mixture of part (a),
    c. mixing 3.5 Kg of sugar into the mixture produced by part (b) and
    d. coating said mixture with a water insoluble compound selected from the group consisting of ethyl cellulose, cellulose acetate butyrate and cellulose triacetate, wherein, said SAK are extracted from fruit of *Momordica charantia* L.

11. A method for lowering blood glucose level comprising administering to a patient in need thereof, an effective amount of the sustained release pharmaceutical composition of claim 1.

* * * * *